US 6,361,170 B1
Mar. 26, 2002

(54) ABERRATION-FREE IMAGING OF THE FUNDUS OF THE HUMAN EYE

(75) Inventor: Josef Bille, Heidelberg (DE)

(73) Assignee: Heidelberg Engineering Optische Messysteme GmbH, Dossenheim (DE)

( * ) Notice: Subject to any disclaimer, the term of this patent is extended or adjusted under 35 U.S.C. 154(b) by 0 days.

(21) Appl. No.: 09/783,479

(22) Filed: Feb. 14, 2001

(51) Int. Cl.⁷ .................................................. A61B 3/10
(52) U.S. Cl. ....................................................... 351/221
(58) Field of Search ............................... 351/205, 206, 351/221; 606/4, 10, 12, 13, 5; 600/318

(56) References Cited

U.S. PATENT DOCUMENTS

| | | |
|---|---|---|
| 4,579,430 A | 4/1986 | Bille |
| 4,781,453 A | 11/1988 | Kobayashi |
| 4,838,679 A * | 6/1989 | Bille ........................... 351/205 |
| 4,848,340 A | 7/1989 | Bille |
| 5,062,702 A | 11/1991 | Bille |
| D330,769 S | 11/1992 | Blaha |
| 5,920,373 A | 7/1999 | Bille |
| 6,050,687 A | 4/2000 | Bille |

* cited by examiner

*Primary Examiner*—George Manuel
(74) *Attorney, Agent, or Firm*—Nydegger & Associates

(57) ABSTRACT

A device and method for aberration-free imaging of the fundus of the human eye includes a light source, an active mirror for directing light from the light source to and from the fundus and imaging units for viewing the fundus. A sensor compares the wavefront reflected from the eye with an aberration-free wavefront to establish an error signal, and the error signal is used to program the active mirror to remove aberrations from the reflected light. Importantly, all of this is done by focusing the light to a focal spot on the fundus which has three dimensional volumetric measurements, i.e. point spread function (PSF), of as small as approximately 2 $\mu$m×2 $\mu$m×20 $\mu$m. The imaging units include an ellipsometer and a fluoroscope, and the light source can be a laser diode or an AP-diode.

20 Claims, 1 Drawing Sheet

ABERRATION-FREE IMAGING OF THE FUNDUS OF THE HUMAN EYE

FIELD OF THE INVENTION

The present invention pertains generally to ophthalmic diagnostic equipment. More particularly, the present invention pertains to devices and methods for examining the fundus of the eye. The present invention is particularly, but not exclusively useful for generating an aberration-free beam of light that can be focused into the fundus with a focal depth of approximately twenty microns.

BACKGROUND OF THE INVENTION

Using an optical device to examine human tissue requires the ability to precisely focus an incident light beam to a predetermined focal spot on the tissue. This can be difficult to accomplish. In the specific case of the fundus of an eye (i.e. the retina), the size of the focal spot that is required for an effective examination is infinitesimal. The task is further complicated by the fact that the light beam must be effectively directed through the eye before it is incident at its focal spot in the fundus.

The anatomy of the fundus of an eye is known to comprise several distinct layers. These layers are of different types of tissue, and in an anterior to posterior direction they include: axons, ganglion cells, bipolar cells, receptors (rods and cones), pigment cells and the choroid. Together, these layers establish a depth for the fundus that is somewhere in the range of about three hundred and fifty microns, plus or minus a hundred microns (350 $\mu$m±100 $\mu$m). Individually, however, some layers are only about twenty microns (20 $\mu$m) in depth (e.g. ganglion cells and pigment cells). Therefore, in order to effectively examine the various layers of the fundus, it is necessary to resolve a volume of tissue having a depth that is equal to or less than 20 $\mu$m. Stated differently, this requires an ability to focus incident light onto a focal pot in the fundus that has a three dimensional point spread function (PSF), i.e. the finest volume to be resolved, that has a twenty micron depth. Optical physics and the anatomical structure of the eye, however, affect the ability to do this.

Whenever a beam of light is focused to a point, it happens that the light beam is cone shaped in the space between the focusing element (e.g. a lens) and the point to which the beam is focused (i.e. a focal spot). In accordance with optical physics, it also happens that the depth of focus at the focal spot will decrease dramatically as the cone angle of the focused light is increased. As indicated above, for fundus examinations, it is desirable to have as shallow a depth for the focal spot as is possible. Consequently, there is a need for relatively large cone angles. For the human eye, however, the cone angle for light that can be focused onto the fundus is limited in at least two ways. For one, the iris of the eye limits the amount of light that can enter the eye. At most, the iris can be dilated to establish an aperture that is only about a six millimeters (6 mm) in diameter. For another, the cornea and lens of the eye introduce significant optical aberrations into the light that is being focused onto the fundus when the aperture is increased beyond about two millimeters (2 mm).

To contrast the consequences for an optical examination of the fundus of a normal eye, it is helpful to appreciate the difference between the possible PSFs for a 2 mm aperture and a 6 mm aperture. With a 2 mm aperture, the PSF is a volume that is approximately 10 $\mu$m×10 $\mu$m×200 $\mu$m. On the other hand, with a 6 mm aperture, a PSF with a volume of 2 $\mu$m×2 $\mu$m×20 $\mu$m, is possible. The assumption here has been that the light being focused is aberration-free. Thus, for optical examinations of the fundus, wherein the depth of the focal spot needs to be limited to about 20 $\mu$m, it is very desirable to be able to use the full 6 mm potential for the aperture of the iris. Additionally, due to differences in the tissues of the retina that are to be imaged, it is desirable to use different imaging modalities. Specifically, blood in tissues of the retina need to be imaged using techniques that are different from the techniques used to image essentially transparent tissue.

In light of the above, it is an object of the present invention to provide a device for imaging the fundus of the human eye which is capable of generating an essentially aberration-free beam of light for use in diagnosing the fundus. It is another object of the present invention to provide a device for imaging the fundus that can effectively focus light into the fundus with a focal depth (i.e. PSF) of about twenty microns. Still another object of the present invention is to provide a device for imaging the fundus of the human eye which is capable of examining individual layers of tissue in the fundus using appropriate imaging modalities. Yet another object of the present invention is to provide a device for imaging the fundus of the human eye that is easy to use, relatively simple to manufacture and comparatively cost effective.

SUMMARY OF THE PREFERRED EMBODIMENTS

In accordance with the present invention, a device for aberration-free imaging of the fundus of the human eye includes, in part, a plurality of imaging units and an active mirror. The imaging units are respectively used for viewing the fundus (i.e. retina) of the eye with different imaging modalities, and the active mirror can be programmed to effectively remove aberrations from the light that is focused onto the fundus and which is subsequently reflected from the fundus and received by the imaging unit. In more detail, the device of the present invention includes a light source for generating a light beam, and there is an optical element for focusing the light beam through the eye to a focal spot in the fundus. The light that is reflected from the focal spot can then be imaged. Depending on the imaging modality, different imaging units will be used to do this. For example, the imaging unit may be a fluoroscope if blood vessels in the retina are to be imaged. On the other hand, the imaging unit may be an ellipsometer if transparent tissue is to be imaged.

Regardless the imaging modality being used, when the light beam is reflected from the focal spot in the fundus, it will exhibit a reflected wavefront that is characteristic of the reflected beam. This reflected wavefront is then directed, by the active mirror, toward the imaging unit. Due to aberrations introduced by the eye, however, the reflected wavefront requires some compensation before it reaches the imaging unit.

In order to compensate the wavefront that is reflected from the fundus of the eye, a computer/comparator is used to compare the reflected wavefront with an aberration-free wavefront (e.g. a plane wavefront). Specifically, this comparison is made to establish an error signal. The computer/comparator then uses the error signal to program the active mirror to accomplish two separate, but interrelated functions. For one, the programmed active mirror compensates for aberrations that are introduced into the light beam before it is incident on the focal point in the fundus. For another, the programmed active mirror compensates the reflected wavefront, to thereby create an aberration-free wavefront that is received by the imaging unit.

It is an important aspect of the present invention that the eye be as widely dilated as possible when the light beam is focused to a focal spot in the fundus and, accordingly, when the light is reflected from the focal spot and received at the imaging unit. Specifically, the aperture of the eye during the operation of the present invention is preferably dilated to about six millimeters in diameter. Normally, the aperture is around two millimeters in diameter. The consequence of this dilation is two-fold. First, the extended aperture (i.e. 6 mm) allows for a much improved point spread function (PSF) for the focal spot. Specifically, PSF is a three dimensional measurement that defines the finest volume of focus for a light beam. It happens that when the aperture of the eye is dilated to about 6 mm, the PSF can be as small as about 2 $\mu$m×2 $\mu$m×20 $\mu$m. In contrast, with a two millimeter diameter aperture for the eye, the PSF is more on the order of 10 $\mu$m×10 $\mu$m×200 $\mu$m. Second, with an extended aperture, significant aberrations are introduced into light as it passes into and out of the eye through the cornea. Nevertheless, in order to effectively image individual layers with the fundus of the eye that may be as shallow as 20 $\mu$m, it is necessary to have the improved PSF with a depth of focus that is around 20 $\mu$m. Thus, the purpose of the present invention is to compensate for the introduced aberrations and, consequently, be able to benefit from the improved PSF.

As envisioned for the present invention, the imaging unit can be any device or apparatus known in the art, such as an ellipsometer or a fluoroscope. Also, the light source can be of any type known in the art, such as a laser diode or a super luminescence diode (SLD).

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
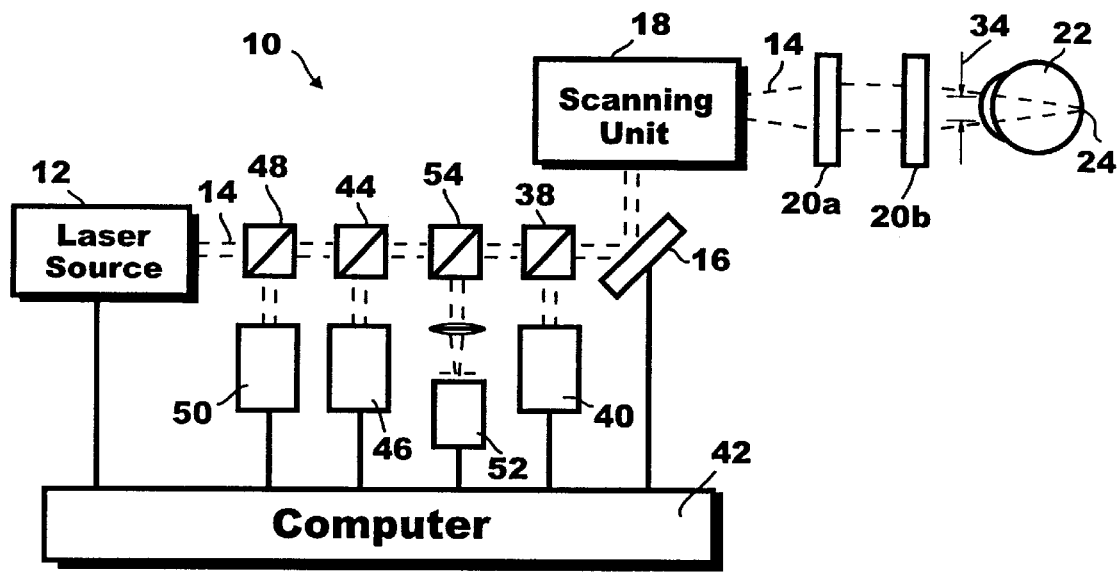
FIG. 1 is a schematic of the device of the present invention showing the interrelationship of its components.

Referring initially to FIG. 1, a device for aberration-free imaging of the fundus of the human eye is shown and generally designated 10. As shown, the device 10 includes a laser source 12 for generating a light beam 14. After leaving the laser source 12, the light beam 14 is turned by an active mirror 16 toward a scanning unit 18. As intended for the present invention, the active mirror 16 is preferably of a type that is disclosed in U.S. application Ser. No. 09/512,440 which was filed on Feb. 25, 2000 for an invention of J. Bille entitled "Method for Programming an Active Mirror to Mimic a Wavefront." As intended for the present invention, the scanning unit 18 may be of any type well known in the art that is capable of directing the light beam 14 along a preselected beam path.

Figure 2:
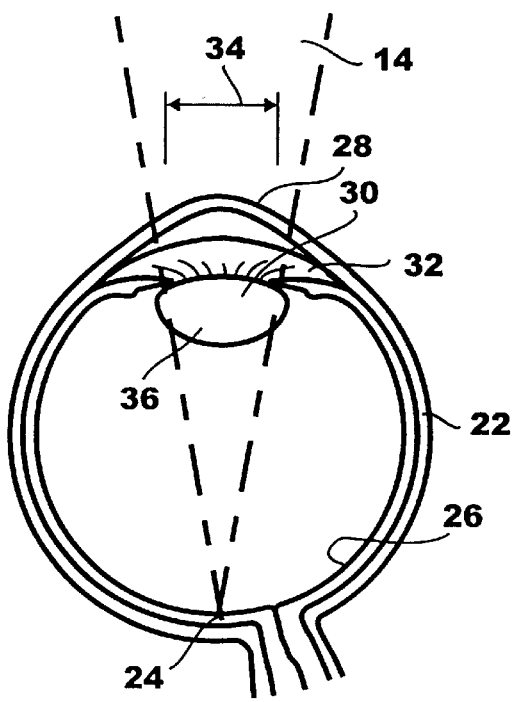
FIG. 2 is an anatomical cross section of a human eye.
Figure 3:
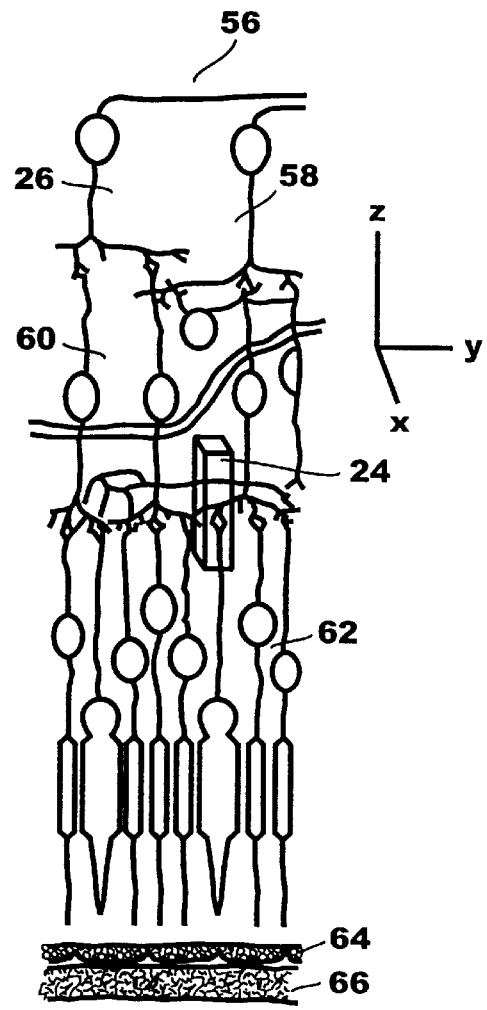
FIG. 3 is a representative illustration of a portion of the fundus of a human eye.

FIG. 1 also shows that the scanning unit 18 operates in concert with focusing lenses 20a and 20b to focus the light beam 14 to a point on the beam path. Specifically, for the present invention, the light beam 14 is to be focused into the eye 22. More specifically, as best seen in FIG. 2, the light beam 14 is focused to a focal spot 24 inside the fundus (retina) 26 of the eye 22. Referring for the moment to FIG. 3, it is to be seen and appreciated that the focal spot 24 is actually a volume of tissue in the fundus 26 into which the light beam 14 is focused. As indicated above, the PSF for this focal spot 24 can be as small as 2 $\mu$m×2 $\mu$m×20 $\mu$m.

Referring to FIG. 2 it is to be appreciated that as the light beam 14 enters the eye 22, it passes through the cornea 28 and through an aperture 30 that is established by the iris 32. For purposes of disclosure, the aperture 30 is generally circular and has a diameter 34 that will increase or decrease depending on the dilation of the eye 22. In any event, after passing through the aperture 30, the light beam 14 then passes through the lens 36 of the eye 22 and is incident at the focal spot 24 in the fundus 26. It happens that as the light beam 14 follows the above-described path, aberrations are introduced into the light beam 14. Most noticeably, the aberrations are introduced into the light beam 14 by the cornea 28. The situation, however, is aggravated when the eye 22 is dilated to the point where the diameter 34 of the aperture 30 is approximately equal to six millimeters. As indicated above, this extended aperture 30 (i.e. diameter 34 is six millimeters) is desirable in order to achieve an effective PSF for the focal spot 24.

It happens that the light will be reflected from the focal spot 24 as though the focal spot 24 is effectively a point source of light. As this reflected light travels back through the eye 22, however, it will be susceptible to the same aberrations just mentioned. Again, for an extended aperture 30, these aberrations can be significant.

Referring back to FIG. 1 it will be appreciated that the light that is reflected from focal spot 24 will be directed for further reflection from the active mirror 16. For purposes of the device 10 of the present invention, a portion of the light that is reflected from the active mirror 16 will then be turned by a beam splitter 38 toward a wavefront sensor 40. Preferably, the wavefront sensor 40 is a Hartmann-Shack type sensor that will effectively describe a reflected wavefront for the light that has been reflected from the focal spot 24. This reflected wavefront will, of course, include the aberrations that were introduced as the light traveled from the eye 22 to the wavefront sensor 40. The reflected wavefront is then analyzed by a computer/comparator 42. Specifically, the computer/comparator 42 compares the reflected wavefront with an aberration-free wavefront (e.g. a plane wavefront) to create an error signal. This error signal is then used to program the active mirror 16. As intended for the present invention, this programming of the active mirror 16 will thereafter introduce changes in the reflected wavefront, as reflected from the focal spot 24, to create an aberration-free wavefront in reflection from the active mirror 16. As contemplated for the present invention, the active mirror 16 can be reprogrammed with a new error signal at a frequency of approximately ten Hertz.

Still referring to FIG. 1, it will be seen that an aberration-free wavefront of the light that is reflected from the focal spot 24 can be selectively directed to various imaging units. For example, depending on the particular imaging purpose, the aberration-free wavefront may be directed by a beam splitter 44 to an imaging unit (ellipsometer) 46. Alternatively, the aberration-free wavefront may be directed by a beam splitter 48 toward an imaging unit (fluoroscope) 50. FIG. 1 also indicates that an avalanche-photo (AP) diode 52 can be used as a reflective microscope confocal with a beam splitter 54 to generate a reflective confocal image of the selected layer within the retina 26. As anticipated by the present invention, the diode 52 can be used together with the active mirror 16 to optimize either the incoming or outgoing light beam 14.

For the operation of the device 10 of the present invention, it is first necessary to dilate the eye 22. Preferably this is done until the diameter 34 of the aperture 30 is approximately six millimeters. The light beam 14 is then directed and focused by the scanning unit 18 and the focusing lenses 20a and 20b to the focal spot 24. For the device 10, the focal spot 24 can be moved through the fundus 26 by the scanning unit 18 and focusing lenses 20a and 20b to view individual layers within the fundus 26.

In FIG. 3 it is to be appreciated that the focal spot 24 is shown generally in scale relative to the fundus 26. Importantly, the z-dimension of the focal spot 24 is approximately twenty microns (20 $\mu$m). Thus, movement of the focal spot 24 through the fundus 26 in the z-direction will allow imaging of the various layers in the fundus 26 because these layers have respective depths in the z-direction which are generally less than 20 $\mu$m. Specifically, the various layers of tissue within the fundus 26 have depths approximately as follows: axons 56 (50–100 $\mu$m), ganglion cells 58 (20 $\mu$m), bipolar cells 60 (50 $\mu$m), receptors 62 (30–50 $\mu$m), pigment cells 64 (20 $\mu$m), and the choroid 66 (100 $\mu$m).

Due to the differences in the characteristics of tissue in the various layers of the fundus 26, different imaging modalities are possible with the present invention. For instance, the imaging of micro blood vessels in the fundus 26, and more specifically, the blood vessels in the choroid 66, are best imaged using fluoroscopic techniques. Such techniques may also be best for imaging receptors 62 and pigment cells 64. Accordingly, the imaging unit 50 will be employed for these purposes. On the other hand, essentially transparent tissue such as is found in the nerve fibers of the axons 56 and ganglion cells 58 may be best imaged using birefringent (polarization) techniques. In this case, the imaging unit (ellipsometer) 46 would be employed.

While the particular Aberration-Free Imaging of the Fundus of the Human Eye as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for aberration-free imaging of the fundus of the human eye which comprises:
    a plurality of imaging units;
    an active mirror;
    a light source for generating an incident light beam, said incident light beam having an incident wavefront;
    an optical element for focusing said incident light beam to a focal spot in the fundus for reflection therefrom as a reflected beam;
    a sensor for determining a reflected wavefront, said reflected wavefront being characteristic of said reflected beam;
    a comparator for comparing said reflected wavefront with an aberration-free wavefront to establish an error signal; and
    a means for programming said active mirror with said error signal to compensate said incident wavefront for focus by said optical element as an aberration-free wavefront to said focal spot in the fundus, and to compensate said reflected wavefront for receipt by said imaging units as an aberration-free wavefront.

2. A device as recited in claim 1 wherein said focal spot has a depth dimension into the fundus and said depth dimension is approximately twenty microns (20 $\mu$m).

3. A device as recited in claim 1 wherein said imaging unit is an ellipsometer.

4. A device as recited in claim 1 wherein said imaging unit is a fluoroscope.

5. A device as recited in claim 1 wherein said imaging unit is a reflective confocal microscope.

6. A device as recited in claim 1 wherein said light source is a laser diode.

7. A device as recited in claim 1 wherein said light source is an SLD diode.

8. A device as recited in claim 1 wherein said aberration-free wavefront is a plane wavefront.

9. A device as recited in claim 1 wherein said programming means establishes closed loop control for said device.

10. A device as recited in claim 9 wherein said error signal is re-established at a frequency of approximately ten hertz (10 Hz).

11. A method for aberration-free imaging of the fundus of the human eye which comprises the steps of:
    dilating the iris of the human eye to create an aperture having an extended diameter;
    directing a light beam with an active mirror through said aperture to a focal spot in the fundus of the human eye for reflection therefrom as a reflected beam;
    determining a reflected wavefront, said reflected wavefront being characteristic of said reflected beam;
    comparing said reflected wavefront with an aberration-free wavefront to establish an error signal; and
    programming said active mirror with said error signal to compensate said reflected wavefront for receipt by an imaging unit as an aberration-free wavefront.

12. A method as recited in claim 11 wherein said extended diameter is approximately six millimeters (6 mm).

13. A method as recited in claim 11 wherein said focal spot has a depth dimension into the fundus and said depth is approximately twenty microns (20 $\mu$m).

14. A method as recited in claim 13 wherein said focal spot has three dimensional volumetric measurements of approximately 2 $\mu$m×2 $\mu$m×20 $\mu$m.

15. A method as recited in claim 11 wherein said imaging unit is an ellipsometer.

16. A method as recited in claim 11 wherein said imaging unit is a fluoroscope.

17. A method as recited in claim 11 wherein said imaging unit is a reflective confocal microscope.

18. A method as recited in claim 11 wherein said light beam is generated by a light source and wherein said light source is a laser diode.

19. A method as recited in claim 11 wherein said light beam is generated by a light source and said light source is an SLD diode.

20. A method as recited in claim 11 wherein said aberration-free wavefront is a plane wavefront.

* * * * *